United States Patent
Tang et al.

(10) Patent No.: US 10,709,934 B2
(45) Date of Patent: Jul. 14, 2020

(54) ROUTE PLANNING METHOD AND WEARABLE DEVICE

(71) Applicant: Huawei Technologies Co., Ltd., Shenzhen (CN)

(72) Inventors: Ruiming Tang, Shenzhen (CN); Xiuqiang He, Shenzhen (CN); Zhenhua Dong, Shenzhen (CN); Zhirong Liu, Shenzhen (CN); Yanjie Li, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 16/540,401

(22) Filed: Aug. 14, 2019

(65) Prior Publication Data

US 2019/0366156 A1    Dec. 5, 2019

Related U.S. Application Data

(63) Continuation of application No. PCT/CN2018/077267, filed on Feb. 26, 2018.

(30) Foreign Application Priority Data

Feb. 28, 2017    (CN) .......................... 2017 1 0115442

(51) Int. Cl.
*H04W 24/00*    (2009.01)
*A63B 24/00*    (2006.01)
(Continued)

(52) U.S. Cl.
CPC ........ *A63B 24/0062* (2013.01); *A61B 5/1118* (2013.01); *A63B 24/0006* (2013.01);
(Continued)

(58) Field of Classification Search
CPC ... A61B 5/1118; A61B 5/681; A61B 5/02438; G06F 1/163; A63B 24/0062;
(Continued)

(56) References Cited

U.S. PATENT DOCUMENTS 7,625,316 B1 * 12/2009 Amsbury ........... A63B 24/0062
                                                                    482/1
2011/0032105 A1    2/2011 Hoffman et al.
(Continued)

FOREIGN PATENT DOCUMENTS

| CN | 105260799 A | 1/2016 |
| CN | 106096794 A | 11/2016 |
| EP | 3109595 A1 | 12/2016 |

OTHER PUBLICATIONS

Foreign Communication From A Counterpart Application, European Application No. 18760340.2, Extended European Search Report dated Dec. 4, 2019, 10 pages.
(Continued)

*Primary Examiner* — Nhan T Le
(74) *Attorney, Agent, or Firm* — Conley Rose, P.C.

(57) ABSTRACT

A route planning method includes obtaining exercise capability information of a wearer and one or more candidate routes, where the candidate routes include attribute features that comprise historical exercise capability information, where the historical exercise capability information is information calculated according to a first preset rule and based on obtained exercise capability information of a plurality of users having exercised along the candidate routes; determining a target route based on the attribute features of the candidate routes and the exercise capability information of the wearer; and outputting the target route information.

20 Claims, 5 Drawing Sheets

(51) Int. Cl.
  *A61B 5/11* (2006.01)
  *G01C 22/00* (2006.01)
  *G06F 1/16* (2006.01)

(52) U.S. Cl.
  CPC .......... *G01C 22/006* (2013.01); *G06F 1/163* (2013.01); *A63B 2024/0009* (2013.01); *A63B 2024/0065* (2013.01)

(58) Field of Classification Search
  CPC .... A63B 2024/0068; A63B 2024/0009; A63B 2024/0065; A63B 24/0006; G01C 22/006
  See application file for complete search history.

(56) References Cited

U.S. PATENT DOCUMENTS

| | | |
|---|---|---|
| 2014/0222330 A1 | 8/2014 | Kohlenberg et al. |
| 2015/0058157 A1 | 2/2015 | Tamir et al. |
| 2016/0209216 A1* | 7/2016 | Naylor ................ G06F 19/3481 |

OTHER PUBLICATIONS

Machine Translation and Abstract of Chinese Publication No. CN105260799, dated Jan. 20, 2016, 11 pages.
Machine Translation and Abstract of Chinese Publication No. CN106096794, dated Nov. 9, 2016, 34 pages.
Cao, M., et al. "Content-based approach to exercise route recommendation, Computer Engineering and Applications," 2016, vol. 52, No. 9, pp. 33-38, with English Abstract.
English Translation of Cao, M., et al. "Content-based approach to exercise route recommendation, Computer Engineering and Applications," 2016, vol. 52, No. 9, 13 pages.
Foreign Communication From A Counterpart Application, PCT Application No. PCT/CN2018/077267, English Translation of International Search Report dated May 21, 2018, 2 pages.
Foreign Communication From A Counterpart Application, PCT Application No. PCT/CN2018/077267, English Translation of Written Opinion dated May 21, 2018, 3 pages.

* cited by examiner

ROUTE PLANNING METHOD AND WEARABLE DEVICE

CROSS-REFERENCE TO RELATED APPLICATIONS

This application is a continuation application of international patent application number PCT/CN2018/077267, filed on Feb. 26, 2018, which claims priority to Chinese Patent Application No. 201710115442.4, filed on Feb. 28, 2017. The disclosures of the aforementioned applications are hereby incorporated by reference in their entireties.

TECHNICAL FIELD

Embodiments of the present disclosure relate to the field of intelligent terminals, and in particular, to a route planning method and a wearable device.

BACKGROUND

With continuous improvement of living standards, people are paying more attention to health and exercise. Running or walking, as a simple but effective type of exercise, is accepted by the masses. Various types of health software are used to track exercise statuses (for example, routes, time periods, speeds, and strength) of users in real time, and provide the users with various services. Relatively commonly, the services include data statistics and exercise plan making.

However, mainstream health wearables in the market do not have a function of recommending an exercise route to a user. Currently, a shortcoming of the service is that because users need to explore the exercise route by themselves, the users cannot find a suitable exercise route within a short time period.

In a solution in other approaches, only simple data statistics or data monitoring can be performed. For various types of health software or various health wearables currently popular in the market, functions mainly include step counting, distance recording, calorie conversion, a clock, sleep monitoring, an alarm clock, short message service notification, Global Positioning System (UPS) positioning, heart rate measurement, reminding, and the like, and there is no exercise route recommendation function. Some wearable devices can output information about a walkable route in a surrounding area of a user, and then the user selects a route for running or walking. In this case, the information that is about the route and that is output by the wearable device only needs to indicate that the route is walkable. Therefore, the information about the route may not be suitable for the user to go running, resulting in poor user experience.

SUMMARY

Embodiments of the present disclosure provide a route planning method and a wearable device, to recommend a suitable exercise route to a wearer, and improve use experience of the wearer.

A first aspect of the embodiments of the present disclosure provides a route planning method. The route planning method includes first obtaining exercise capability information of a wearer and one or more candidate routes, where the exercise capability information of the wearer refers to historical exercise parameters of the wearer, for example, information such as an average rate, an average heart rate, and average blood pressure obtained when the wearer does exercise, the one or more candidate routes are routes along which exercise can be done and that are within a preset range based on a position of the wearer, the one or more candidate routes include attribute features of the routes, the attribute features include historical exercise capability information, the historical exercise capability information is information calculated according to a first preset rule and based on obtained exercise capability information of a plurality of users having exercised along the one or more candidate routes, exercise capability information corresponding to a route refers to exercise parameters obtained after a historical user does exercise on the route, for example, parameter information such as an average exercise rate, an average heart rate, and average blood pressure of the historical user on the route, and the attribute features of the routes include the historical exercise capability information, and further include basic information of the one or more candidate routes, for example, basic information such as a length, an altitude, and a gradient; and then determining a target route based on the attribute features of the one or more candidate routes and the exercise capability information of the wearer, where historical exercise capability information corresponding to the target route and the exercise capability information of the wearer have a highest matching degree, or routes whose historical exercise capability information has highest matching degrees with the exercise capability information of the wearer are candidate target routes, and the plurality of matching degrees are matching degrees of historical exercise capability information corresponding to a plurality of one or more candidate routes and the exercise capability information of the wearer. Therefore, there may be one or more target routes. After the target route is determined, the target route information is output.

In this way, a target route recommended for a wearer is determined in combination with a personal exercise capability of the wearer and attribute features of a plurality of candidate routes, such that the recommended target route meets a basic exercise requirement of the wearer, thereby improving exercise experience of the wearer.

In a possible implementation, after the obtaining exercise capability information of a wearer and one or more candidate routes, the method may further include dividing the one or more candidate routes into k subroutes according to a second preset rule, where a division rule may be performing division based on a fixed length, for example, a segment of every 50 meters is used as a subroute; or may be performing division based on a fixed quantity of subroutes, for example, the one or more candidate routes are evenly divided into 10 subroutes based on a total length of the one or more candidate routes; or may be performing division based on gradients of the one or more candidate routes, for example, a subroute having a gradient greater than 30 degrees in the one or more candidate routes is obtained through separate division; then calculating an attribute feature of each subroute after obtaining the subroutes through division; and finally outputting the target route information including the attribute features of the subroutes of the target route. For example, the output target route is a route A with a total length of 1000 meters, an average rate is 8 kilometers per hour, an average heart rate is 135 times per minute, and an average temperature is 38.5 degrees centigrade. The target route includes a subroute having a gradient greater than 30 degrees, a length of the subroute is 100 meters, an average rate is 5 kilometers per hour, an average heart rate is 145 times per minute, and an average temperature is 39 degrees centigrade. In this way, the wearer can select or determine the target route based on more specific information thereof.

If the wearer does not intend to run on a route having a gradient, the wearer may select another route to do exercise, thereby improving user experience.

In another possible implementation, before the determining a target route based on the attribute features of the one or more candidate routes and the exercise capability information of the wearer, the method may further include obtaining exercise requirement information of the wearer, where the exercise requirement information is information input by the wearer. The determining a target route based on the attribute features of the one or more candidate routes and the exercise capability information of the wearer includes determining the target route based on the attribute features of the one or more candidate routes, the exercise capability information of the wearer, and the exercise requirement information of the wearer.

If the wearer has a specific exercise requirement before doing exercise, the wearer may input the exercise requirement information in advance. In this way, comprehensive recommendation is performed in combination with the exercise requirement information input by the wearer and the exercise capability information, thereby improving use experience of a user.

In another possible implementation, before the determining a target route based on the attribute features of the one or more candidate routes and the exercise capability information of the wearer, the method may further include obtaining environment information at a first moment, where the first moment is a moment before the wearer does exercise. The determining a target route based on the attribute features of the one or more candidate routes and the exercise capability information of the wearer includes determining the target route based on the attribute features of the one or more candidate routes, the exercise capability information of the wearer, and the environment information at the first moment.

In this implementation, before route planning, the environment information such as a route congestion condition and a weather condition before the wearer does exercise may further be obtained, thereby performing more preferable recommendation.

In another possible implementation, the method may further include obtaining environment information at a second moment, where the second moment is a moment at which the wearer does exercise; and determining, based on the environment information at the second moment, whether to adjust the target route selected by the wearer, and outputting adjustment indication information if determining, based on the environment information at the second moment, to adjust the target route selected by the wearer.

It should be noted that the second moment may be understood as a moment in an exercise process of the wearer.

In this implementation, if an incident happens in the exercise process of the wearer due to, for example, weather such as a rainstorm and a typhoon, or an anthropogenic reason such as a riot near a route. In this case, an adjustment indication may be output. Specific adjustment may be performed based on completion of the exercise done by the wearer. For example, if a completion degree is 90% in a light rain, the adjustment is accelerating the completion or ending in advance. If a significant incident such as a riot happens nearby, the adjustment is recommending a safe return route, for the wearer to immediately return safely.

A second aspect of the embodiments of the present disclosure provides a wearable device, including a first obtaining unit configured to obtain exercise capability information of a wearer and one or more candidate routes, where the one or more candidate routes include attribute features of the routes, the attribute features include historical exercise capability information, and the historical exercise capability information is information calculated according to a first preset rule and based on obtained exercise capability information of a plurality of users having exercised along the one or more candidate routes; a determining unit configured to determine a target route based on the attribute features of the one or more candidate routes and the exercise capability information of the wearer; and an output unit configured to output the target route information.

In another possible implementation, the wearable device further includes a dividing unit configured to divide the one or more candidate routes into k subroutes according to a second preset rule after the first obtaining unit obtains the exercise capability information of the wearer and the one or more candidate routes; and a calculation unit configured to calculate an attribute feature of each subroute; and the output unit is further configured to output the target route information including the attribute features of the subroutes.

In another possible implementation, the first obtaining unit is further configured to obtain exercise requirement information of the wearer before the determining unit determines the target route based on the attribute features of the one or more candidate routes and the exercise capability information of the wearer, where the exercise requirement information is information input by the wearer; and the determining unit is further configured to determine the target route based on the attribute features of the one or more candidate routes, the exercise capability information of the wearer, and the exercise requirement information of the wearer.

In another possible implementation, the wearable device further includes a second obtaining unit configured to obtain environment information at a first moment before the determining unit determines the target route based on the attribute features of the one or more candidate routes and the exercise capability information of the wearer, where the first moment is a moment before the wearer does exercise; and the determining unit is further configured to determine the target route based on the attribute features of the one or more candidate routes, the exercise capability information of the wearer, and the environment information at the first moment.

In another possible implementation, the wearable device further a second obtaining unit configured to obtain environment information at a second moment, where the second moment is a moment at which the wearer does exercise; and a judging unit configured to determine, based on the environment information at the second moment, whether to adjust the target route selected by the wearer; and the output unit is further configured to output adjustment indication information when the judging unit determines to adjust the target route selected by the wearer.

A third aspect of the embodiments of the present disclosure provides a wearable device. The apparatus includes a processor, a memory, and a transceiver. The processor, the memory, and the transceiver are connected by using a bus. The memory stores a computer instruction. The processor executes the computer instruction to implement the following method including obtaining exercise capability information of a wearer and one or more candidate routes, where the one or more candidate routes include attribute features of the routes, the attribute features include historical exercise capability information, and the historical exercise capability information is information calculated according to a first preset rule and based on obtained exercise capability information of a plurality of users having exercised along the one or more candidate routes; determining a target route based on the attribute features of the one or more candidate routes and the exercise capability information of the wearer; and outputting the target route information.

A fourth aspect of the embodiments of the present disclosure provides a storage medium. The storage medium stores a computer instruction for implementing the route planning method in the first aspect.

A fifth aspect of the embodiments of the present disclosure provides a computer program product. The computer program product includes a computer software instruction. The computer software instruction may be loaded by using a processor to implement a procedure in the route planning method according to any one of the first aspect or the possible implementations of the first aspect.

It can be learned from the foregoing technical solutions that the embodiments of the present disclosure have the following advantages.

In the embodiments of the present disclosure, the exercise capability information of the wearer and the one or more candidate routes are first obtained. The one or more candidate routes include the attribute features including the historical exercise capability information. The historical exercise capability information is information calculated based on the obtained exercise capability information of the plurality of users having exercised along the one or more candidate routes and according to the first preset rule. In addition, the target route is determined based on the attribute features of the one or more candidate routes and the exercise capability information of the wearer. Finally, the target route information is output. In this way, a target route recommended for a wearer is determined in combination with a personal exercise capability of the wearer and attribute features of a plurality of candidate routes, such that the recommended target route meets a basic exercise requirement of the wearer, thereby improving exercise experience of the wearer.

DESCRIPTION OF EMBODIMENTS

Embodiments of the present disclosure provide a route planning method and a wearable device, to recommend a suitable exercise route to a wearer, and improve use experience of the wearer.

Figure 1:
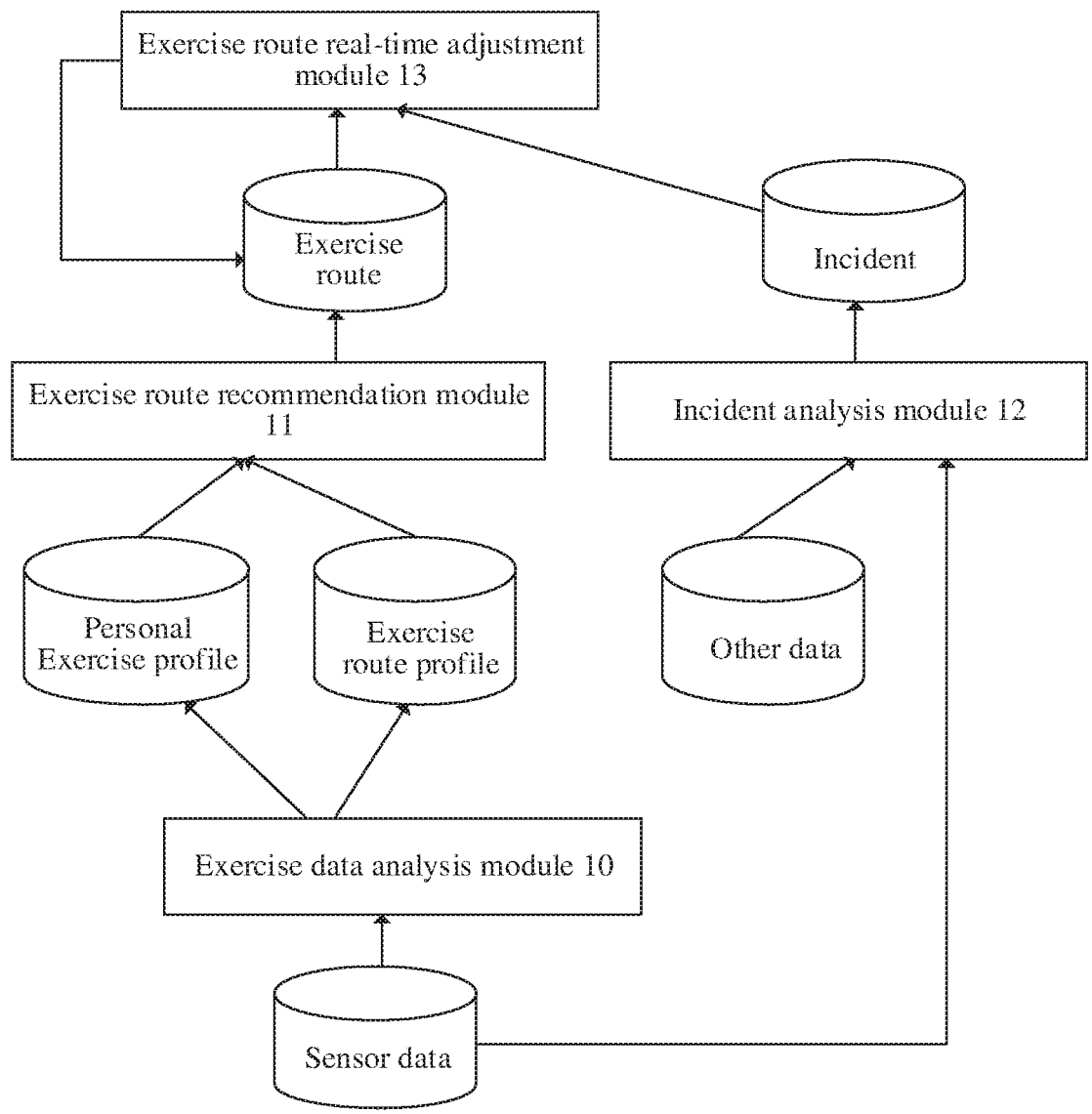
FIG. 1 is a schematic diagram of a system architecture to which a route planning method is applied according to an embodiment of the present disclosure.

FIG. 1 is a schematic diagram of a system architecture to which a route planning method is applied according to an embodiment of the present disclosure. The system architecture includes an exercise data analysis module 10, an exercise route recommendation module 11, an incident analysis module 12, and an exercise route real-time adjustment module 13. The function modules are described as follows.

The exercise data analysis module 10 is configured to obtain exercise capability information of a wearer and candidate route information based on data collected by a wearable device. The exercise capability information includes a personal exercise profile of the wearer. The candidate route information includes exercise route profiles. The personal exercise profile includes an exercise-related feature or attribute of the user, for example, includes static features such as a gender, a height, and a weight, and an exercise capability of the user. The exercise capability includes information such as an average heart rate and average blood pressure during exercise. The exercise route profile includes information such as a length, an altitude, and a gradient of a route, average time that is in historical data and that is spent by a plurality of users to complete exercise on the route, and average heart rate that are in the historical data and that are of the plurality of users during exercise on the route.

The exercise route recommendation module 11 recommends, based on the personal exercise profile and the candidate exercise route profiles that are obtained by the exercise data analysis module 10, and environment information collected by the wearable device, M most suitable exercise routes from candidate routes to the user for selection, where M is a positive integer greater than or equal to 1.

The incident analysis module 12 determines, based on other data sources (for example, traffic data, weather data, and news data) and user information and the environment information that are collected by the wearable device of the user, whether an incident occurs.

The exercise route real-time adjustment module 13 adjusts a current exercise route in real time based on the exercise routes recommended by the exercise route recommendation module 11 and the incident analyzed by the incident analysis module 12.

It should be noted that, during specific application, functions of some of the modules may be implemented by the wearable device, and functions of the other modules are implemented by another user device such as a mobile phone. Then the mobile phone sends an implementation result of the modules to the wearable device, or the mobile phone directly outputs an implementation result of the modules. In addition, alternatively, functions of all the modules may be implemented by the wearable device. This is not limited herein.

An example in which the functions of all the modules are implemented by the wearable device is used below to describe a specific embodiment of the route planning method in this embodiment of the present disclosure.

Figure 2:
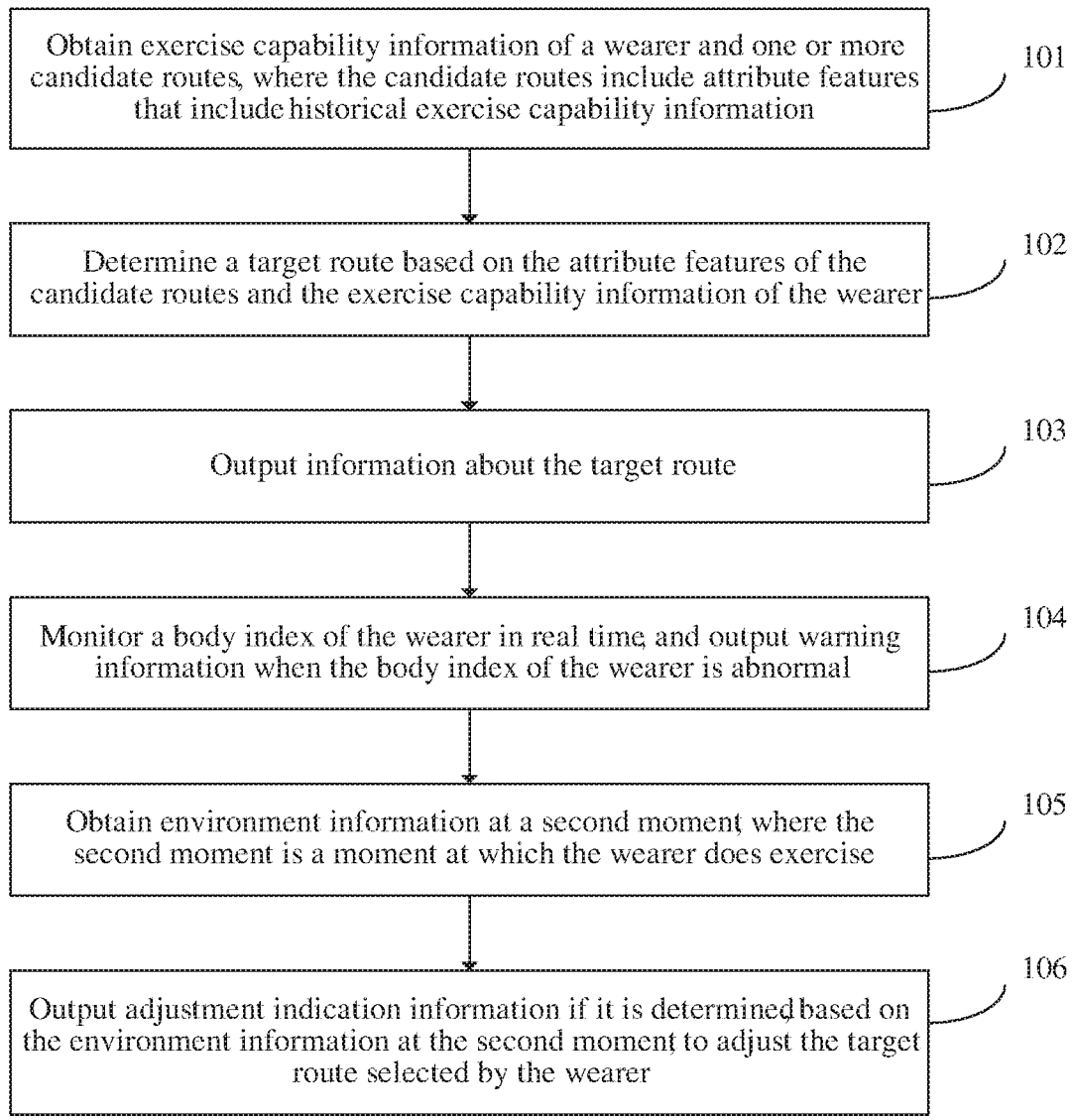
FIG. 2 is a schematic diagram of an embodiment of a route planning method according to embodiments of the present disclosure.

FIG. 2 is a schematic diagram of an embodiment of a route planning method according to the embodiments of the present disclosure. The method is performed by a wearable device, and further includes the following steps.

101: Obtain exercise capability information of a wearer and one or more candidate routes, where the one or more candidate routes include attribute features that include historical exercise capability information, and the historical exercise capability information is information calculated according to a first preset rule and based on obtained exercise capability information of a plurality of users having exercised along the one or more candidate routes.

For example, the exercise data analysis module 10 in FIG. 1 in this embodiment of the present disclosure, first needs to obtain the exercise capability information of the wearer, that is, the personal exercise profile in FIG. 1, and further needs to obtain a plurality of candidate routes. The plurality of candidate routes include attribute features that include historical exercise capability information, that is, the exercise route profiles in the embodiment in FIG. 1. For an obtaining manner of the candidate routes, positioning may be performed on the wearable device, and then candidate routes within a preset range of the wearable device and suitable for running or walking may be selected in combination with historical user exercise data.

Forming of the personal exercise profile further includes exercise feature defining, user exercise route processing, and user exercise route feature aggregation. The exercise feature defining means defining a feature that is of the personal exercise profile and that is used to describe an exercise capability of the user. For example, the exercise feature defining is represented by using an expression $u_{sport}=<usp_1, usp_2, \ldots, usp_m>$, where $u_{sport}$ is used to represent an exercise feature of a user u, $usp_1$ is used to represent a first exercise feature of the user u, and $usp_m$ is used to represent an $m^{th}$ exercise feature of the user u. For example, a personal exercise feature of the user u may be $usp_i \in$ {a speed, blood pressure, a heart rate, a skin temperature, a blood oxygen level, consumed calories . . . }.

The user exercise route processing means processing feature data of exercise routes of a historical user. The data of the exercise routes is first extracted based on the defined exercise feature. A historical exercise route set of the user u is defined as history_route(u). Each route r in the set meets a condition r∈history_route(u). The defined $u_{sport}$ is extracted from the routes. For example, $u_{sport}$={a speed, a heart rate, and a skin temperature}. For each historical route of a user, an average speed, an average heart rate, and an average skin temperature of the user during historical exercise on the route are extracted. For example, a piece of processed user exercise route data is (8 km/hour, 135/min, 38.5° C.), and a set of processed user exercise routes is represented as history_route_transform(u).

The user exercise route feature aggregation means performing an aggregation operation on the set of processed user exercise routes, to obtain a user exercise profile. For example, the user has two pieces of user route data, (8 kilometer (km)/hour, 135/min, 38.5 degree celsius (° C.) and (6 km/hour, 145/min, 39.5° C.). Assuming that an aggregation function is an average function, the user exercise profile is represented as (7 km/hour, 140/min, 39° C.). After the user exercise route feature aggregation, a depiction of the personal exercise profile of the user is formed. The personal exercise profile directly reflects the exercise capability information of the user.

In addition, demographic attributes such as gender, age, and occupation of the user may further be added to the personal exercise profile, to more precisely depict the exercise capability of the user, and more deeply reflect a body index of the user, thereby facilitating subsequent personalized route recommendation.

The exercise route profile is further formed through route feature defining and historical user exercise feature aggregation. The route feature defining means defining a feature that is of an exercise route and that affects exercise of the user. For example, the exercise route profile is represented by using an expression $r_{sport}=<rsp_1, rsp_2, \ldots, rsp_n>$, where $r_{sport}$ represents the route profile of the route, $rsp_1$ represents a first feature, and $rsp_n$ represents an $n^{th}$ feature. For example, a route feature of a route is $rsp_i \in$ {a length, a speed, consumed calorie, a gradient, an altitude . . . }. It should be noted that the route feature of the route includes exercise features of the route, such as a speed, consumed calories, a heart rate, and blood pressure, and further includes attributes of the route, for example, features such as a length, a position, a gradient, and an altitude.

The historical user exercise feature aggregation means first obtaining personal exercise features of a user who already does exercise on the route, extracting features affecting exercise of the user, such as a speed, consumed calories, a heart rate, blood pressure, and a skin temperature, and then aggregating the extracted features by using an aggregation function, for example, obtaining by using an average function, an average speed, average consumed calories, an average heart rate, average blood pressure, an average skin temperature, and the like when the historical user does exercise on the route. In addition, aggregation of statistics about male and female may further be performed respectively by using gender features of historical users. In this way, a depiction of an exercise route profile of a route is formed. The exercise route profile directly reflects exercise capability information corresponding to the route.

Optionally, each exercise route may further be divided into subroutes. To be specific, each exercise route r is divided into k subroutes. Attribute features of each subroute r' include a static feature and an exercise feature. The static feature (for example, a length, a gradient, and an altitude) may be directly recorded. The exercise feature is obtained by aggregating exercise features corresponding to a large quantity of users. For example, an exercise speed on a subroute needs to be obtained. Exercise speeds of three users on the subroute are 8 km/hour, 9 km/hour, and 10 km/hour. If an average function is used, the exercise speed on the subroute is 9 km/hour. A route may be divided into subroutes based on a fixed preset length, or based on a total length of the route and a fixed quantity of subroutes, or based on a gradient of the route in reality. Details are not limited. Subroute division and reflection of attribute features of subroutes can more practically present a specific condition of the route. For example, an overall average gradient of a route is 20 degrees, but the route includes a subroute having a gradient of 50 degrees. If a user does not intend to run on a route having an excessively high gradient when doing exercise, the user may observe attribute features of subroutes of the route, to avoid selecting the route having an excessively high gradient to do exercise, thereby improving exercise experience of the user.

102: Determine a target route based on the attribute features of the one or more candidate routes and the exercise capability information of the wearer.

Figure 3:
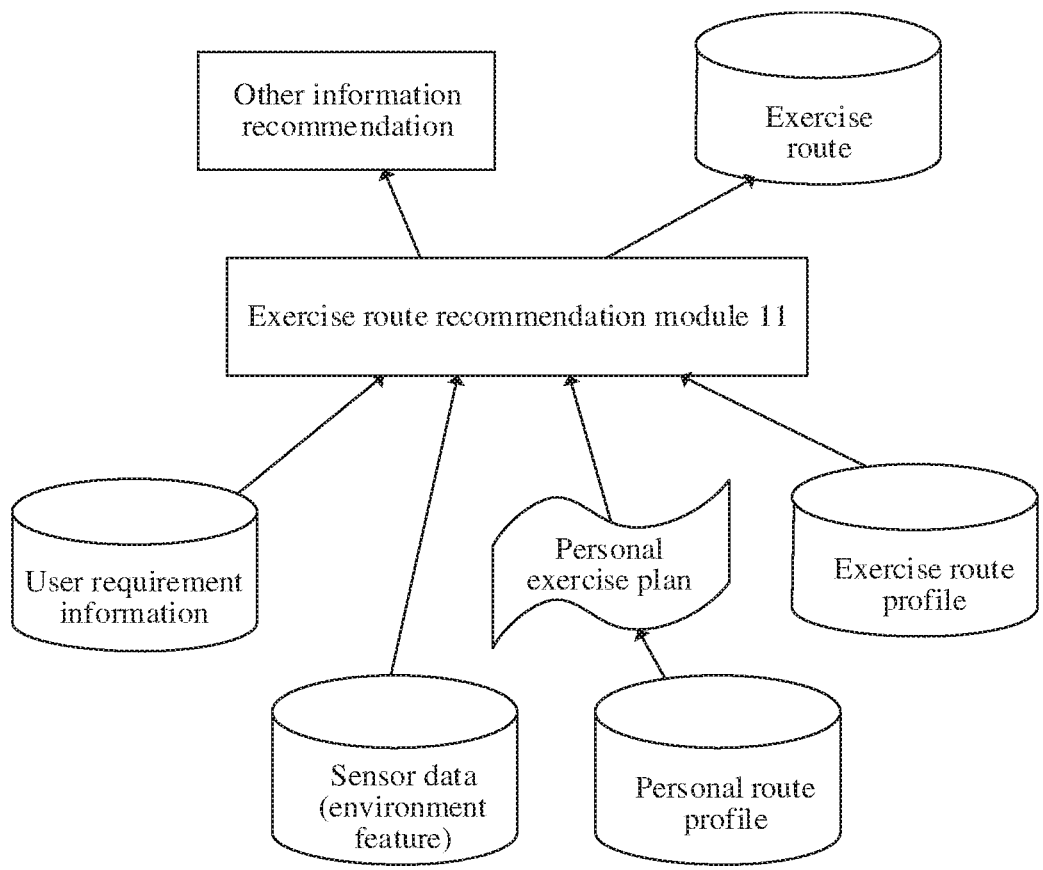
FIG. 3 is a schematic diagram of a framework of an exercise route recommendation module according to an embodiment of the present disclosure.

FIG. 3 is a schematic diagram of a framework of an exercise route recommendation module. The module is configured to implement a function of the exercise route recommendation module 11 in FIG. 1. After the exercise capability information of the wearer and the one or more candidate routes are obtained in step 101, the attribute features of the candidate routes already match the exercise capability information of the wearer, such that a route having a high matching degree in the plurality of candidate routes may be determined as the target route. The attribute features of the candidate routes are the exercise route profiles described in the foregoing step. The exercise capability information of the wearer is the personal exercise profile described in the foregoing step. The exercise route profiles and the personal exercise profile have same exercise features. For example, the exercise route profiles include a speed, a heart rate, blood pressure, a skin temperature, and consumed calories, and the personal exercise profile also includes a speed, a heart rate, blood pressure, a skin temperature, and consumed calories. In this way, same features are matched, such that a route having a highest exercise capability matching degree with the personal exercise profile of the wearer is selected from the plurality of candidate routes, thereby using the route having the highest matching degree as the candidate route. Alternatively, area range division may be performed based on the features in the personal exercise profile of the wearer. For example, the speed in the personal exercise profile of the wearer is 8 km/hour, the heart rate is 135/min, the blood pressure is 190 mmHg, the skin temperature is 39° C., and the consumed calcifies are 120 calories. Then the area range division is performed based on the features in the personal exercise profile of the wearer, thereby determining a route in the candidate routes that has feature values in a divided area range as the target route. For example, the area range may be divided with a speed of 7 km/hour to 9 km/hour, a heart rate of 125/min to 145/min, blood pressure of 180 mmHg to 200 mmHg, and a skin temperature of 38.5° C. to 39.5° C. Provided that an area of an exercise feature of a candidate route in an exercise profile is within the defined area, the corresponding candidate route may be used as the target route. Therefore, there may alternatively be a plurality of target routes.

Optionally, the target route may alternatively be determined by using a model obtained through machine learning training. A data source of the model may be obtained by using exercise capability information of historical users and use experience of the historical users. For example, when selecting a route, most historical users are more inclined to select a route having a high matching degree with heart rates of the users. This represents that when the historical users select the route, a heart rate is a more important feature. Therefore, matching of the feature, the heart rate, may be adjusted in the model to a scoring item having a higher weight. For another example, when selecting a route, most historical users are further inclined to select a route having a high matching degree with blood pressure of the users. This represents that when the historical users select the route, the blood pressure is also an important feature. Therefore, matching of the feature, the blood pressure, may be adjusted in the model to a scoring item having a higher weight. Weight scoring is performed on all features of routes through such training learning, thereby sorting the routes based on scoring results, and finally selecting a route having a highest score as the target route, or selecting top five routes having highest scores as target routes. It should be noted that herein, a target route is recommended in the model training manner is merely a target route determining manner in this embodiment of the present disclosure. During an embodiment application, the target route may alternatively be determined in another model training manner. Details are not limited.

Optionally, an advanced exercise plan mode is further set in the wearable device. If the wearer is in a steady stage of an advanced personal exercise plan, during featuring matching, the wearer selects a route by selecting a more smooth area. If the wearer is in a challenge stage of the advanced personal exercise plan, the wearer intensifies some features, for example, an exercise mode, exercise intensity, and exercise duration. Relatively high areas are set for such features to select a route. For example, if a personal exercise plan made by the wearer is intensive training, the wearable device may perform intensive recommendation based on a historical exercise record of the wearer. For example, the last exercise distance is 1000 meters, and a body temperature during exercise is 38.5 degrees centigrade. During current recommendation and planning, a route corresponding to a distance greater than 1200 meters and a body temperature during exercise greater than 38.7 degrees centigrade may be recommended. In this way, exercise intensity on the recommended route is greater than that on a route selected by the wearer last time. Alternatively, if the personal exercise plan made by the wearer is steady training, the wearable device may perform steady recommendation based on a historical exercise record of the wearer. For example, the last exercise distance is 1000 meters, and a body temperature during exercise is 38.5 degrees centigrade. During current recommendation and planning, a route corresponding to a distance in a range of 900 to 1100 meters may be recommended, and a body temperature during exercise on the route is in a range of 38.2 to 38.7 degrees centigrade. In this way, intensity on the recommended route is almost the same as that on a route selected by the wearer last time, such that the wearer does exercise more purposefully, and the exercise has more effects.

Optionally, before the determining a target route, this embodiment of the present disclosure may further include the following step such as obtaining exercise requirement information of the wearer, where the exercise requirement information is information input by the wearer. The determining a target route is further determining the target route based on the attribute features of the candidate routes, the exercise capability information of the wearer, and the exercise requirement information of the wearer.

The wearer may further input, based on a personal requirement of the wearer, personal requirement information by using a mobile phone or directly on the wearable device. The requirement information may be requirement information of route features, for example, a start position and a final position of a route, a total exercise length, an exercise time period, an altitude, and a route safety degree. In addition, the wearer may further input requirement information such as exercise intensity. For example, it is required that a speed on the route is at least 10 kilometers per hour, and an altitude is at least 200 meters. It should be rioted that when the requirement information input by the wearer includes an exercise feature such as a speed, when the target route is determined by screening the candidate routes based on the attribute features of the candidate routes, the exercise capability information of the wearer, and the exercise requirement information of the wearer, limited matching screening is performed by using the exercise requirement information of the wearer a high priority.

Optionally, before the determining a target route, this embodiment of the present disclosure may further include the following step such as obtaining environment information at a first moment, where the first moment is a moment before the wearer does exercise. The determining a target route is further determining the target route based on the attribute features of the candidate routes, the exercise capability information of the wearer, and the environment information at the first moment.

Before the target route is determined, current environment information may further be obtained. The environment information includes environment features, for example, a current temperature, weather, humidity, a wind speed, and a current time point. In this embodiment of the present disclosure, the target route may alternatively be determined in combination with the currently obtained environment information, the attribute, features of the candidate routes, and the exercise capability information of the wearer. For example, the current wind speed is relatively large, a relatively short route may be preferably selected, to avoid a trouble of returning midway due to a rain. Alternatively, it is 10 o'clock in the evening, a route on which there is a relatively large quantity of people currently may be preferably selected, to improve safety during running in the evening, and so on. The current environment information may be obtained by using a sensor of the wearable device, by accessing the Internet, by connecting to a mobile phone, or the like. This is not limited herein.

Optionally, in this embodiment of the present disclosure, the target route may alternatively be determined in combination with the currently obtained environment information, the attribute features of the candidate routes, the exercise capability information of the wearer, and the exercise requirement information input by the wearer.

Optionally, this embodiment of the present disclosure may further include the following step such as outputting device recommendation information and material supplement recommendation information based on the exercise capability information of the wearer, an attribute feature of the target route, and the environment information at the first moment.

The device recommendation information may be sports clothes, shoes, a cap, and other apparatuses. For example, there is a light rain currently, and recommendation information of sports clothes and a sports cap that are worn during raining may be output. For example, if average calories consumed by the wearer are relatively high, a current temperature is relatively high, recommendation information such as water supplement may be output to the wearer, such that the user can do exercise more safely.

103: Output the target route information.

If there is one determined target route, related information of the target route is output, including attribute feature information of the target route. If there are a plurality of determined target routes, the plurality of determined target routes may be sorted by using a preset model. The preset model may include experience scores of historical users for the plurality of target routes, and may further include weight scores of exercise features on the routes, thereby obtaining a scoring result of each target route. Then, the target routes are sorted in descending order and output based on the scoring results. The wearer autonomously performs selection. In addition, the target routes may further be strategically presented and output. For example, historical scores of the wearer for some target routes are relatively low, and the target routes are not output. Alternatively, if the plurality of target routes include a route on which the wearer never does exercise, the route may be preferably output and presented, to improve novelty to the user.

Optionally, when there are a plurality of determined target routes, this embodiment of the present disclosure further includes the following steps such as receiving a first operation instruction, where the first operation instruction is a selection instruction operation performed by the wearer on a plurality of target routes; and displaying, according to the first operation instruction, the target route selected by the wearer, and updating the attribute feature of the target route based on the exercise capability information of the wearer.

After the wearer selects a target route, the wearer becomes a historical user of the selected target route. Therefore, the attribute feature of the target route is updated based on the exercise capability information of the wearer, such that more data support is subsequently provided for another user, thereby better recommending a route. It should be noted that the updating herein does not mean updating the attribute feature of the target route based on information about exercise capabilities of all wearers, and may mean selective updating, for example, increasing 1 to a quantity of people currently doing exercise on the target route, and updating an average age of the historical users. After the wearer completes exercise, after the wearable device collects statistics about exercise features such as a speed and a heart rate when the wearer does exercise on the target route, the wearable device updates an exercise feature of the target route based on the personal exercise features.

Optionally, if determining the target route in step 102 is performed by using a model obtained through the machine learning training, after the wearer selects a target route, the wearer becomes a historical user. The wearable device may update the model based on a selection action of the wearer and attribute information of the corresponding selected target route, thereby training data in the model, and improving model applicability.

Optionally, this embodiment of the present disclosure may further include the following step.

104: Monitor a body index of the wearer in real time, and output warning information when the body index of the wearer is abnormal.

In this embodiment of the present disclosure, the body index of the wearer may further be detected by using the wearable device in real time. For example, body index information such as a heart rate, blood pressure, and a skin temperature of the wearer is detected by using the sensor of the wearable device. When an abnormality occurs in the body indexes, for example, the heart rate is excessively high, or the blood pressure is excessively high, warning information may be output. The warning information may display or output through a voice a specific body index of the wearer having an abnormality, and prompts the wearer to rest or take other treatment measures.

In addition, the wearable device may further monitor, using an apparatus such as a sensor or a gyroscope, whether the wearer falls to the ground. If the wearable device detects that the wearer falls to the ground, and detects that an abnormality occurs in the body indexes of the wearer, a communications apparatus of the wearable device may directly communicate with a communications apparatus of an emergency contact, and send abnormal information of the wearer to the communications apparatus of the emergency contact.

When detecting that an abnormality occurs in the body indexes of the wearer, the wearable device may further adjust the target route. For example, if detecting that a skin temperature of the wearer is excessively high, the wearable device may adjust the target route to a route to a rest stop closest to the wearable device.

Optionally, this embodiment of the present disclosure may further include the following step.

105: Obtain environment information at a second moment, where the second moment is a moment at which the wearer does exercise.

When the wearer does exercise on the selected target route, the wearable device may further obtain current environment information based on a preset period or in real time, for example, whether it begins to rain, whether a current temperature suddenly drops, whether there is a traffic jam, or whether a riot happens on the target route. These environment factors directly affect exercise experience of the wearer. Therefore, the wearer may obtain the current environment information even though the wearer is doing exercise. The wearable device may obtain the environment information by accessing the Internet, or from a mobile phone terminal, or from a wearable device of another user who currently does exercise on the target route. Details are not limited.

Figure 4:
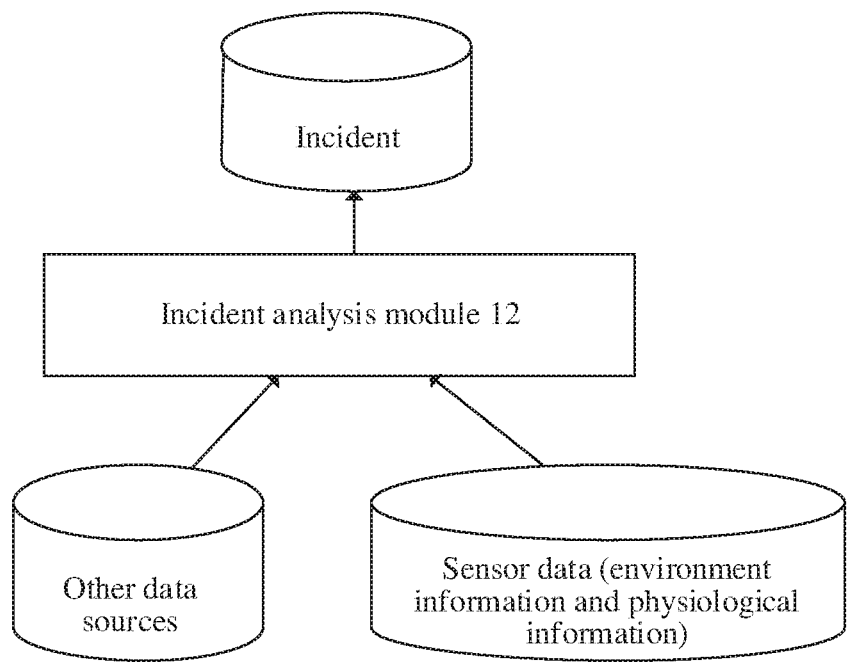
FIG. 4 is a schematic diagram of a framework of an incident analysis module according to an embodiment of the present disclosure.

The environment information obtained when the wearer does exercise and the body indexes detected when the wearer does exercise are both likely to cause an incident. FIG. 4 is a schematic diagram of a framework of an incident analysis module. After obtaining data from a plurality of data sources, the incident analysis module analyzes and determines, using a preset threshold range, whether an event is defined as an incident.

106: Output adjustment indication information if it is determined, based on the environment information at the second moment, to adjust the target route selected by the wearer.

Figure 5:
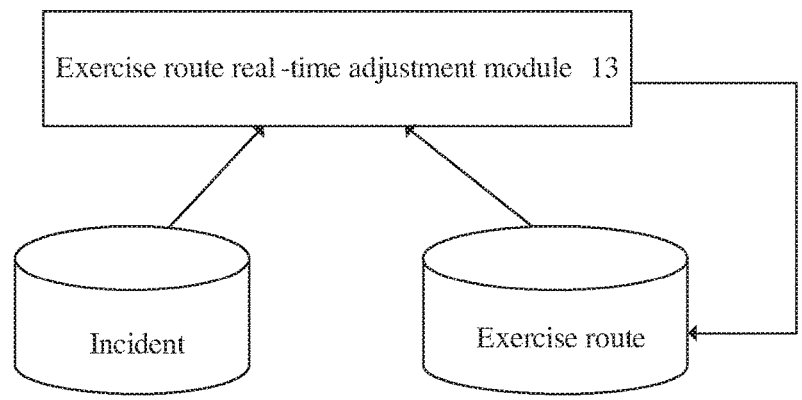
FIG. 5 is a schematic diagram of a framework of an exercise route real-time adjustment module according to an embodiment of the present disclosure.

FIG. 5 is a schematic diagram of a framework of an exercise route real-time adjustment module. After the current environment information is obtained, whether a preset threshold is reached is determined based on the environment information. If the preset threshold is reached, the adjustment indication information of the target route is output. A possible adjustment solution is accelerating or decelerating to complete the current route; changing a route and completing exercise; giving up exercise and moving to a closest safe place; or giving up exercise and returning by the way the wearer comes. A most proper adjustment solution is selected based on completion on the current route and a severity level of an incident (not limited to the following rules).

When the exercise route has been almost completed and the incident is not very severe, an original route may be insisted on, but an exercise speed is suggested to be changed.

When most of the exercise route has not been completed and the incident is not very severe, another exercise route may be selected from the candidate routes to adjust the current route.

When most of the exercise route has not been completed much and the incident is very severe, the user may be suggested to give up the current exercise route and return by the way the user comes.

When the exercise route has been almost completed and the incident is very severe, the user may be suggested to give up exercise and move to a closest safe place.

After reading the adjustment indication information, the wearer may determine, according to an adjustment indication, how to adjust the target route, to complete current exercise, thereby improving exercise experience of the user.

Optionally, after completing exercise, the wearer may further perform a scoring operation on the selected target route according to an operation instruction. Therefore, the wearable device may further receive the operation instruction, and update the attribute feature of the target route according to the operation instruction and based on a scoring result. In this way, the wearable device recommends a more preferable route to the user next time.

It should be noted that in this embodiment of the present disclosure, the wearable device may store the exercise capability information of the wearer and information about attribute features of all routes, thereby performing route planning recommendation, or may not store the exercise capability information of the wearer and information about attribute features of all routes, but may be associated with a mobile phone terminal or cloud, thereby obtaining the exercise capability information of the wearer and attribute feature information of a related route.

Figure 6:
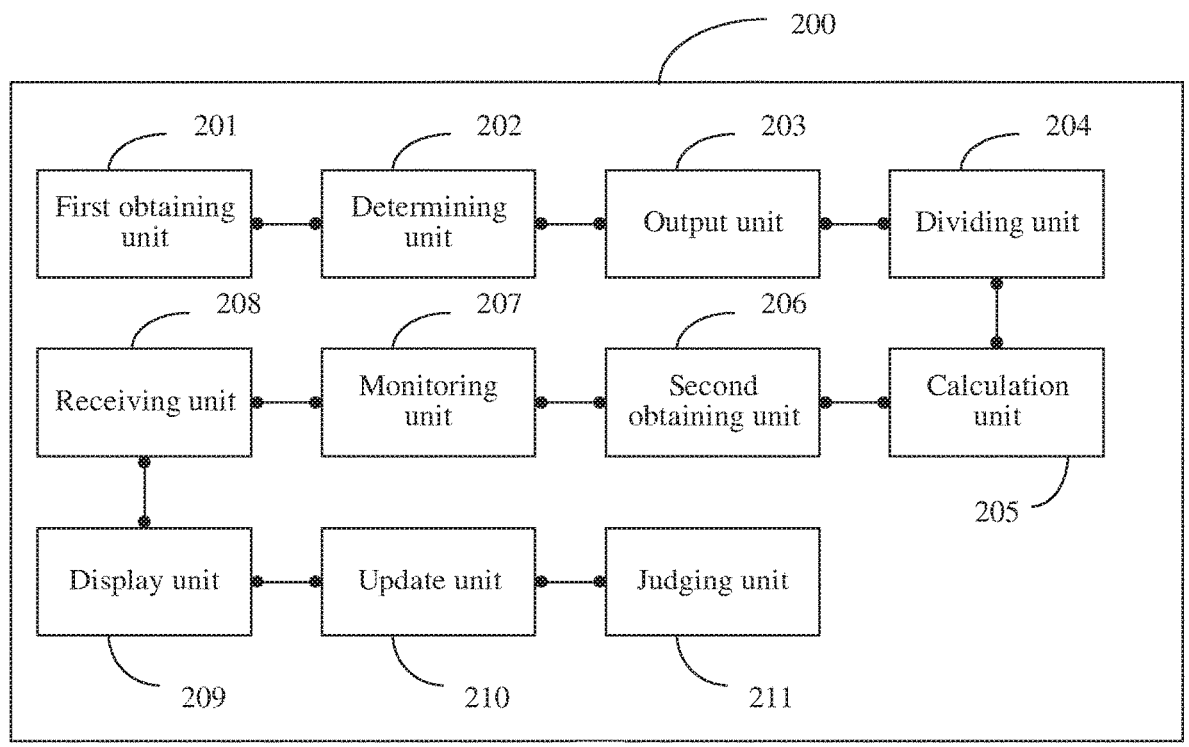
FIG. 6 is a schematic diagram of an embodiment of a wearable device according to the embodiments of the present disclosure.

Referring to FIG. 6, an embodiment of a wearable device 200 in the embodiments of the present disclosure includes a first obtaining unit 201 configured to obtain exercise capability information of a wearer and one or more candidate routes, where the one or more candidate routes include attribute features of the routes, the attribute features include historical exercise capability information, and the historical exercise capability information is information calculated according to a first preset rule and based on obtained exercise capability information of a plurality of users having exercised along the one or more candidate routes; a determining unit 202 configured to determine, a target route based on the attribute features of the candidate routes and the exercise capability information of the wearer; and an output unit 203 configured to output the target route information.

Optionally, the wearable device further includes a dividing unit 204 configured to divide the candidate routes into k subroutes according to a second preset rule after the first obtaining unit obtains the exercise capability information of the wearer and the candidate routes; and a calculation unit 205 configured to calculate an attribute feature of each subroute.

The output unit 203 is further configured to output the target route information including the attribute features of the subroutes.

Optionally, the first obtaining unit 201 is configured to obtain exercise requirement information of the wearer before the determining unit 202 determines the target route based on the attribute features of the candidate routes and the exercise capability information of the wearer, where the exercise requirement information is information input by the wearer.

The determining unit 202 is further configured to determine the target route based on the attribute features of the candidate routes, the exercise capability information of the wearer, and the exercise requirement information of the wearer.

Optionally, the wearable device further includes a second obtaining unit 206 configured to obtain environment information at a first moment before the determining unit 202 determines the target route based on the attribute features of the candidate routes and the exercise capability information of the wearer, where the first moment is a moment before the wearer does exercise.

The determining unit 202 is further configured to determine the target route based on the attribute features of the candidate routes, the exercise capability information of the wearer, and the environment information at the first moment.

Optionally, the wearable device further includes a monitoring unit 207 configured to monitor a body index of the wearer in real time.

The output unit 203 is further configured to output warning information when the body index of the wearer is abnormal.

Optionally, the wearable device further includes a receiving unit 208 configured to receive a first operation instruction after the output unit 203 outputs the target route information, where the first operation instruction is a selection instruction operation performed by the wearer on a plurality of target routes; a display unit 209 configured to display, according to the first operation instruction, the target route selected by the wearer; and an update unit 210 configured to update the attribute feature of the target route based on the exercise capability information of the wearer.

Optionally, the output unit 203 is further configured to output device recommendation information and material supplement recommendation information based on the exercise capability information of the wearer, an attribute feature of the target route, and the environment information at the first moment after the second obtaining unit 206 obtains the environment information at the first moment.

Optionally, the second obtaining unit 206 is further configured to obtain environment information at a second moment, where the second moment is a moment at which the wearer does exercise.

A judging unit 211 is configured to determine, based on the environment information at the second moment, whether to adjust the target route selected by the wearer.

The output unit 203 is further configured to output adjustment indication information when the judging unit determines to adjust the target route selected by the wearer.

Optionally, the receiving unit 208 is further configured to receive a second operation instruction, where the second operation instruction is a scoring operation performed by the wearer on the selected target route after completion of the exercise.

The update unit 209 is configured to update the attribute feature of the target route according to the second operation instruction and based on a scoring result.

For specific descriptions of functions of the units in the embodiment in FIG. 6 and an optional embodiment of FIG. 6, refer to further described content of the recommendation method in FIG. 2 to FIG. 5. Details are not described herein again.

Figure 7:
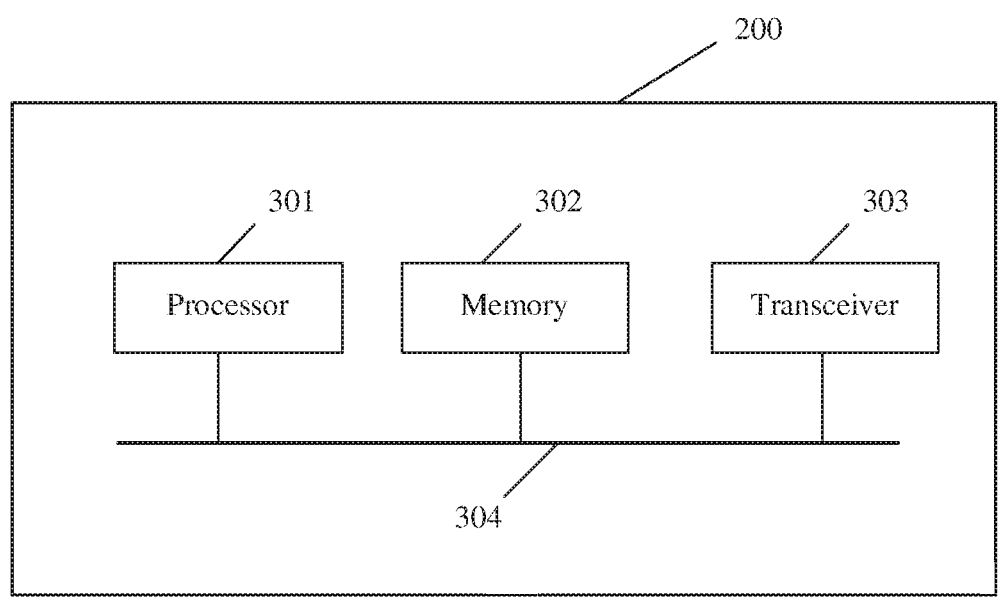
FIG. 7 is a schematic diagram of another embodiment of a wearable device according to the embodiments of the present disclosure.

The wearable device 200 in the embodiment in FIG. 6 further has an embodiment in another form. Referring to FIG. 7, the wearable device 200 includes a processor 301, a memory 302, and a transceiver 303. The processor 301, the memory 302, and the transceiver 303 are connected by using a bus 304. The transceiver 303 may include a transmitter and a receiver. The memory 302 stores a computer instruction. The processor 301 executes the computer instruction to implement a procedure of the route planning method in the embodiment in FIG. 2. Various flexible design manners may be used during specific implementation. For corresponding functions of devices, further refer to the method embodiment. This is not limited in this embodiment of the present disclosure.

All or some of the foregoing embodiments may be implemented by using software, hardware, firmware, or any combination thereof. When software is used to implement the embodiments, the embodiments may be implemented completely or partially in a form of a computer program product.

The computer program product includes one or more computer instructions. When the computer program instructions are loaded and executed on a computer, the procedure or functions according to the embodiments of this application are completely or partially generated. The computer may be a general-purpose computer, a dedicated computer, a computer network, or other programmable apparatuses. The computer instructions may be stored in a computer-readable storage medium or may be transmitted from one computer-readable storage medium to another computer-readable storage medium. For example, the computer instructions may be transmitted from a website, computer, server, or data center to another website, computer, server, or data center in a wired (for example, a coaxial cable, an optical fiber, or a digital subscriber line (DSL)) or wireless (for example, infrared, radio, or microwave) manner. The computer-readable storage medium may be any usable medium accessible by the computer, or a data storage device, such as a server or a data center, integrating one or more usable media. The usable medium may be a magnetic medium (for example, a floppy disc, a hard disk, or a magnetic tape), an optical medium (for example, a DVD), a semiconductor medium (for example, a solid state disk (SSD)), or the like.

In the several embodiments provided in this application, it should be understood at the disclosed system, apparatus, and method may be implemented in other manners. For example, the described apparatus embodiment is merely an example. For example, the unit division is merely logical function division and may be other division during an embodiment implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected based on actual requirements to achieve the objectives of the solutions of the embodiments.

In addition, functional units in the embodiments of this application may be integrated into one processing unit, or each of the units may exist alone physically, or two or more units are integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage medium. Based on such an understanding, the technical solutions of this application essentially, or the part contributing to other approaches, or all or some of the technical solutions may be implemented in the form of a software product. The software product is stored in a storage medium and includes several instructions for instructing a computer device (which may be a personal computer, a server, or a network device) to perform all or some of the steps of the methods described in the embodiments of this application. The foregoing storage medium includes any medium that can store program code, such as a universal serial bus (USB) flash drive, a removable hard disk, a read-only memory (ROM), a random access memory (RAM), a magnetic disk, or an optical disc.

What is claimed is:

1. A route planning method applied to a wearable device, wherein the method comprises:

obtaining historical exercise capability information according to a first preset rule;

obtaining exercise capability information of a wearer of the wearable device and information for a plurality of candidate routes, wherein the information comprises attribute features of the candidate routes comprising the historical exercise capability information, wherein the historical exercise capability information is based on exercise capability information of a plurality of users that have exercised along the candidate routes;

determining a target route based on the attribute features and the exercise capability information of the wearer;

outputting the target route to permit selection of the target route on the wearable device;
monitoring a body index of the wearer in real time; and
outputting warning information when the body index is abnormal.

2. The method of claim 1, further comprising:
dividing the candidate routes into k subroutes according to a second preset rule;
calculating an attribute feature of each subroute of the k subroutes; and
outputting the target route with the attribute feature of the each subroute.

3. The method of claim 1, further comprising:
obtaining exercise requirement information of the wearer; and
determining the target route based on the exercise requirement information of the wearer.

4. The method of claim 1, further comprising:
obtaining environment information at a first moment, wherein the first moment is a moment before the wearer exercises with the wearable device; and
determining the target route based on the environment information at the first moment.

5. The method of claim 4, further comprising outputting device recommendation information and material supplement recommendation information based on the exercise capability information of the wearer, an attribute feature of the target route, and the environment information at the first moment.

6. The method of claim 1, wherein after outputting the target route, the method further comprises:
receiving a first operation instruction comprising a selection instruction operation that is performed on a plurality of target routes;
displaying, according to the first operation instruction, the target route that is selected on the wearable device; and
updating the attribute feature of the target route based on the exercise capability information of the wearer.

7. The method of claim 6, further comprising:
obtaining environment information at a second moment, wherein the second moment is a moment at which the wearer exercises with the wearable device;
determining, based on the environment information at the second moment, whether to adjust the target route that is selected on the wearable device; and
outputting adjustment indication information based on determining to adjust the target route that is selected on the wearable device.

8. The method of claim 1, further comprising:
completing an exercise with the wearable device;
receiving a second operation instruction comprising a scoring operation performed on the target route after completing the exercise; and
updating, according to the second operation instruction, the attribute feature of the target route based on a scoring result.

9. A wearable device, comprising:
a memory configured to store computer instructions; and
a processor coupled to the memory and configured to execute the computer instructions, wherein the computer instructions cause the processor to be configured to:
obtain historical exercise capability information according to a first preset rule;
obtain exercise capability information of a wearer of the wearable device and information for a plurality of candidate routes, wherein the information comprises attribute features of the candidate routes comprising the historical exercise capability information, wherein the historical exercise capability information is based on exercise capability information of a plurality of users that have exercised along the candidate routes;
determine a target route based on the attribute features and the exercise capability information of the wearer;
output the target route to permit selection of the target route on the wearable device;
monitor a body index of the wearer in real time; and
output warning information when the body index is abnormal.

10. The wearable device of claim 9, wherein the computer instructions further cause the processor to be configured to:
divide the candidate routes into k subroutes according to a second preset rule; and
calculate an attribute feature of each subroute of the k subroutes; and
output the target route with the attribute feature of the each subroute.

11. The wearable device of claim 9, wherein the computer instructions further cause the processor to be configured to:
obtain exercise requirement information of the wearer; and
determine the target route based on the exercise requirement information of the wearer.

12. The wearable device of claim 9, wherein the computer instructions further cause the processor to be configured to:
obtain environment information at a first moment, wherein the first moment is a moment before the wearer exercises with the wearable device; and
determine the target route based on the environment information at the first moment.

13. The wearable device of claim 12, wherein the computer instructions further cause the processor to be configured to output device recommendation information and material supplement recommendation information based on the exercise capability information of the wearer, an attribute feature of the target route, and the environment information at the first moment.

14. The wearable device of claim 9, further comprising a display coupled to the memory and the processor, wherein the computer instructions further cause the processor to be configured to:
receive a first operation instruction after outputting the target route, wherein the first operation instruction is a selection instruction operation that is performed on a plurality of target routes; and
update the attribute feature of the target route based on the exercise capability information of the wearer, and wherein the display is configured to display, according to the first operation instruction, the target route selected by the wearer.

15. The wearable device of claim 14, wherein the computer instructions further cause the processor to be configured to:
obtain environment information at a second moment, wherein the second moment is a moment at which the wearer does exercise;
determine, based on the environment information at the second moment, whether to adjust the target route that is selected on the wearable device; and
output adjustment indication information based on a determination to adjust the target route that is selected.

16. The wearable device of claim 9, wherein the computer instructions further cause the processor to be configured to:
 complete an exercise with the wearable device;
 receive a second operation instruction comprising a scoring operation performed on the target route after completing the exercise; and
 update, according to the second operation instruction, the attribute feature of the target route based on a scoring result.

17. A non-transitory computer readable storage medium comprising instructions that, when executed by a processor, cause the processor to:
 obtain historical exercise capability information according to a first preset rule;
 obtain exercise capability information of a wearer of a wearable device and information for a plurality of candidate routes, wherein the information comprises attribute features of the candidate routes comprising the historical exercise capability information, wherein the historical exercise capability information is based on exercise capability information of a plurality of users that have exercised along the candidate routes;
 determine a target route based on the attribute features and the exercise capability information of the wearer;
 output the target route to permit the wearer to select the target route
 monitor a body index of the wearer in real time; and
 output warning information when the body index is abnormal.

18. The non-transitory computer readable storage medium of claim 17, wherein the instructions further cause the processor to:
 obtain exercise requirement information of the wearer; and
 determine the target route based on the exercise requirement information of the wearer.

19. The non-transitory computer readable storage medium of claim 17, wherein the instructions further cause the processor to:
 divide the candidate routes into k subroutes according to a second preset rule;
 calculate an attribute feature of each subroute of the k subroutes; and
 output the target route with the attribute feature of the each subroute.

20. The non-transitory computer readable storage medium of claim 17, wherein the instructions further cause the processor to output device recommendation information and material supplement recommendation information based on the exercise capability information of the wearer, an attribute feature of the target route, and the environment information at the first moment.

* * * * *